United States Patent
Wheeler

(10) Patent No.: US 9,423,331 B2
(45) Date of Patent: Aug. 23, 2016

(54) METHOD OF DETERMINING THE ENERGY CONTENT OF A METHANE-RICH GAS MIXTURE

(75) Inventor: Simon Patrick Hunter Wheeler, Erie, CO (US)

(73) Assignee: Mobrey Limited, Berkshire (GB)

( * ) Notice: Subject to any disclaimer, the term of this patent is extended or adjusted under 35 U.S.C. 154(b) by 768 days.

(21) Appl. No.: 13/640,647

(22) PCT Filed: Apr. 13, 2011

(86) PCT No.: PCT/GB2011/000578
§ 371 (c)(1),
(2), (4) Date: Dec. 28, 2012

(87) PCT Pub. No.: WO2011/128643
PCT Pub. Date: Oct. 20, 2011

(65) Prior Publication Data
US 2013/0138361 A1 May 30, 2013

(51) Int. Cl.
*G01N 9/00* (2006.01)
*G06F 17/10* (2006.01)
*G01N 33/22* (2006.01)

(52) U.S. Cl.
CPC ............. *G01N 9/00* (2013.01); *G01N 33/225* (2013.01); *G06F 17/10* (2013.01)

(58) Field of Classification Search
CPC ............ G01N 9/00; G01N 9/04; G01N 9/26; G01N 9/266; G01N 9/32; G01N 9/36; G06F 17/10
See application file for complete search history.

(56) References Cited

U.S. PATENT DOCUMENTS 4,170,894 A * 10/1979 Zupanick ............... 73/24.05
4,246,773 A    1/1981 Haruta
2005/0143937 A1 6/2005 Morrow et al.

FOREIGN PATENT DOCUMENTS

| EP | 0 939 317 A2 | 9/1999 |
|---|---|---|
| GB | 2 333 371 A | 7/1999 |
| WO | 02/40992 A1 | 5/2002 |

OTHER PUBLICATIONS

International Search Report for PCT Application No. PCT/GB2011/000578, dated Aug. 8, 2011, 5 pages.
Written Opinion for International Search Report for PCT Application No. PCT/GB2011/000578, dated Aug. 8, 2011, 7 pages.
Micro Motion: "Micro Motion 3098 Gas Specific Gravity Meter", Apr. 1, 2009, Micro Motion, XP002652172, Emerson Process Management, pp. 1-8, 8 total pages.

* cited by examiner

*Primary Examiner* — Toan Le
(74) *Attorney, Agent, or Firm* — Westman, Champlin & Koehler, P.A.

(57) ABSTRACT

A method of determining energy content using a specific gravity meter double calibrated to measure both molecular weight and relative density.

12 Claims, 3 Drawing Sheets

| Field | $\rho_{base}$ | %Methane | %Ethane | %Propane | %Iso-butane | %n-butane | %neo-pentane | %n-pentane | %Iso-pentane | %C6+ | %Helium | %CO$_2$ | %N$_2$ |
|---|---|---|---|---|---|---|---|---|---|---|---|---|---|
| Dorsten BTG | 0.8372 | 81.8788 | 2.5359 | 0.4206 | 0.0828 | 0.0679 | 0.0039 | 0.0137 | 0.0187 | 0.0478 | 0.0661 | 1.9842 | 12.8773 |
| Paffrath I | 0.8266 | 84.2727 | 3.4483 | 0.6269 | 0.1052 | 0.1344 | 0.0056 | 0.0387 | 0.0385 | 0.0929 | 0.0553 | 1.4697 | 9.7118 |
| Vreden | 0.8280 | 84.0435 | 3.5863 | 0.6470 | 0.1090 | 0.1376 | 0.0056 | 0.0379 | 0.0377 | 0.0851 | 0.0536 | 1.4739 | 9.7828 |
| Emsburen | 0.8246 | 82.5416 | 2.5260 | 0.5558 | 0.0551 | 0.0626 | 0.0071 | 0.0151 | 0.0156 | 0.0531 | 0.0481 | 0.8285 | 13.5114 |
| Paffrath H | 0.8011 | 89.8040 | 5.5653 | 1.1078 | 0.2820 | 0.1803 | 0.0039 | 0.0328 | 0.0565 | 0.0990 | 0.0192 | 0.7249 | 2.1243 |
| Von Bunde | 0.7996 | 90.1704 | 5.7062 | 1.1423 | 0.2900 | 0.1821 | 0.0036 | 0.0321 | 0.0571 | 0.0982 | 0.0174 | 0.7146 | 1.5860 |
| Waldhaus | 0.7297 | 98.3216 | 0.5187 | 0.1585 | 0.0244 | 0.0296 | 0.0013 | 0.0054 | 0.0066 | 0.0082 | 0.0133 | 0.0815 | 0.8309 |

FIG. 3

METHOD OF DETERMINING THE ENERGY CONTENT OF A METHANE-RICH GAS MIXTURE

CROSS-REFERENCE TO RELATED APPLICATION

This Application is a Section 371 National Stage Application of International Application No. PCT/GB2011/000578, filed Apr. 13, 2011 and published as WO 2011/128643 on Oct. 20, 2011, in English, the contents of which are hereby incorporated by reference in their entirety.

FIELD OF THE INVENTION

This invention relates to energy measurement and, in particular, to a novel method for determining the calorific, value and associated parameters, of methane-rich gases. In this context, a methane-rich gas is a gas having a methane content of greater than 50%.

BACKGROUND TO THE INVENTION

The billing, custody transfer and usage of methane-rich gases, such as natural gas, fuel gas and bio-gas, is heavily dependent upon the energy content of the gas itself—i.e the amount of energy generated upon its combustion.

Energy, often measured in British thermal units (btu), is thus a critical measurement for gas suppliers, transporters and users alike. In addition to this, a parameter associated with the energy generated by the combustion of a gas (called calorific value or CV) is that of Wobbe Index (WI). This is an important parameter that indicates the ease with which a gas will burn.

The American Gas Association (AGA), in their Report No. 5, proposed a formula for the calculation of CV which has been broadly accepted and adopted. This formula is:

$$CV=0.02035+(0.00197-[0.000329 \times Mco2+0.000217 \times Mn2])/SG$$

where Mco2=% $CO_2$ content; Mn2=% $N_2$ content and SG is specific gravity.

For methane rich gases, there are two types of instrumentation that are commonly used to calculate/measure CV or WI—Gas Chromatographs (GC's) and Wobbe Index (WI) meters. GCs provide a relatively slow measurement technique in which the gas is separated into its constituent components and then the gas parameters are calculated by knowing the properties of the individual gases in the mixture. Wobbe Index meters either burn the gas and measure the energy released; or calculate CV or WI through one of a number of non-combustion techniques. For the non-combustion Wobbe Index meters, the major problem encountered during the measurement is that of understanding and accounting for the percentage of inert gases in the methane-rich mixture. Inert gases drastically change the energy content generated by the overall mixture, and thus need to be measured accurately.

GCs are widely used in the gas measurement industry as they are well established and are based on a known measurement method. Whilst they do output the full gas composition, and can calculate gas properties of interest to the user—such as density, base density, CV, WI, specific gravity (SG) etc—they have a number of significant limitations which include:

1. GCs are expensive to buy and have a number of moving parts which can give rise to significant servicing and calibration overhead costs;
2. Calibration gases that mimic the gas to be measured must be generated and this inevitably involves further expense;
3. Calibrations must be repeated typically every 6 to 8 weeks;
4. Skilled, trained operators are required to keep GCs functional & useful; and
5. GCs have a slow response time. Typically an answer is provided every 7 minutes however customers are requiring updates every 5 to 10 secs.

Given this situation, if an alternative method can be found to calculate CV, WI, density, base density, SG etc, then significant opportunities exist in natural gas and fuel gas applications where fast gas energy measurement is required.

It is an object of the invention to provide a method which will go at least some way to addressing the limitations set forth above; or which will at least provide a novel and useful alternative.

SUMMARY OF THE INVENTION

In one aspect the invention provides a method of determining the energy content of a methane-rich gas said method being characterized in that it includes using a specific gravity meter calibrated to measure both molecular weight and relative density.

Preferably said method involves application of the expression:

$$CV=0.02035+(0.00197-[0.000329 \times Mco2+0.000217 \times Mn2])/SG$$

where CV is calorific value; Mco2=% $CO_2$ content; Mn2=% $N_2$ content and SG is specific gravity; or any revision thereof.

Preferably said method further includes using the measured relative density and molecular weight to derive the nitrogen content of said methane-rich gas.

Preferably the method includes deriving nitrogen content according to the expression:

$$\% N_2 = A + B \times \rho_{base} + C \times Z_{base} + D \times M + E \times \% CO_2$$

where: $\rho_{base}$ is base density, $Z_{base}$ is base compressibility, M is molecular weight and A, B, C, D & E are constants.

Alternatively, if % $O_2$ data is available, said method includes deriving nitrogen content according to the expression:

$$\% N_2 = A + B \times \rho_{base} + C \times Z_{base} + D \times M + E \times \% CO_2 + F \times \% O_2$$

where: $\rho_{base}$ is base density, $Z_{base}$ is base compressibility, M is molecular weight and A, B, C, D, E & F are constants.

Preferably the constants A, B, C, D, E and, if applicable, F are determined from historical data obtained from varied sources of methane—rich gas.

Preferably the constant A is refined from time to time using a sampling technique which reduces said methane-rich gas into its constituent parts.

Preferably said method includes determining % carbon dioxide content using a near infrared meter.

Many variations in the way the present invention can be performed will present themselves to those skilled in the art. The description which follows is intended as an illustration only of one means of performing the invention and the lack of description of variants or equivalents should not be regarded as limiting. Wherever possible, a description of a specific element should be deemed to include any and all equivalents thereof whether in existence now or in the future.

BRIEF DESCRIPTION OF THE DRAWINGS

A working embodiment of the invention will now be described with reference to the accompanying drawing in which:

FIG. 3: shows a table of data from which an expression is derived for the calculation of $N_2$ content.

DETAILED DESCRIPTION OF WORKING EMBODIMENT

Figure 1:
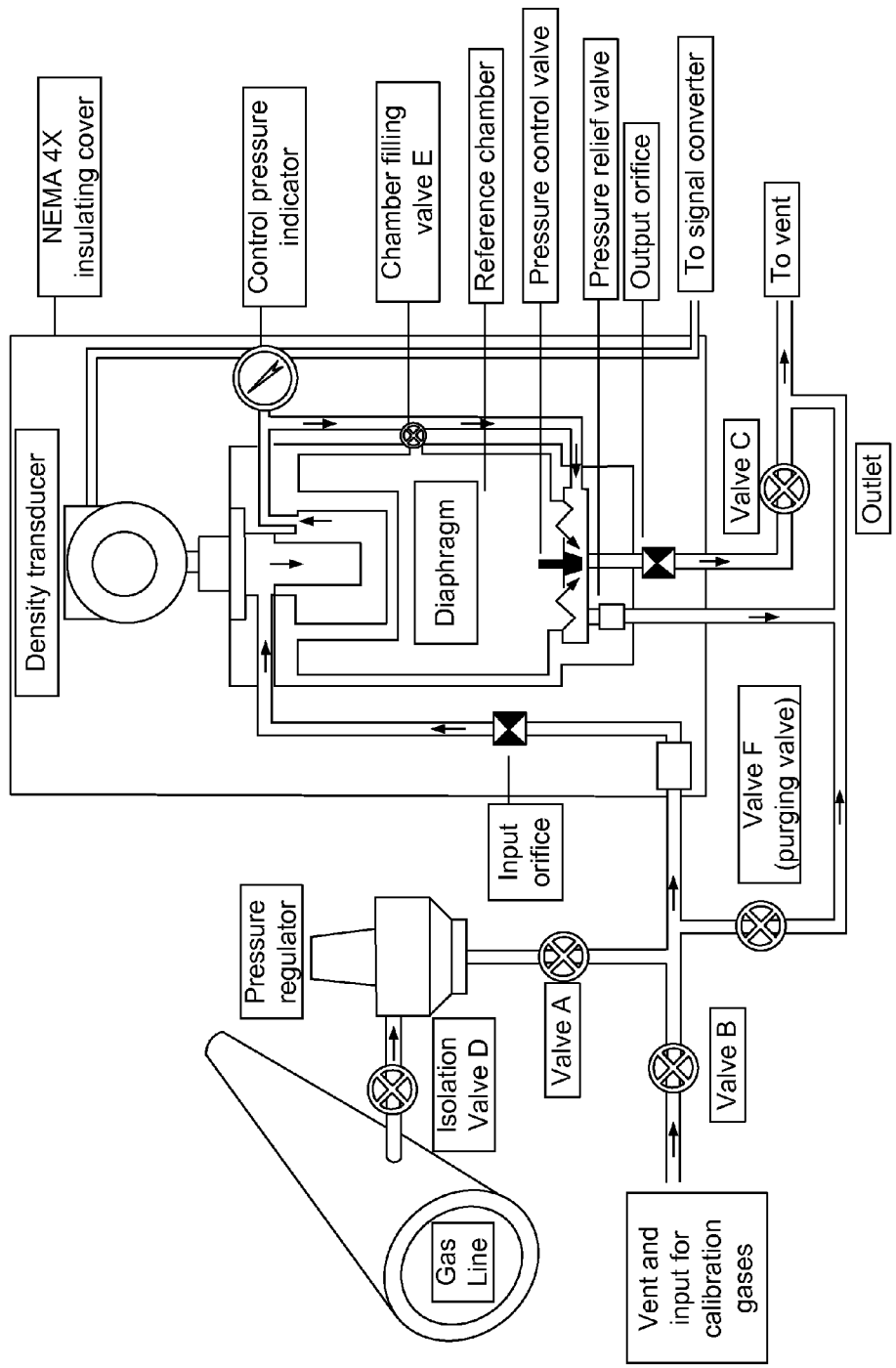
FIG. 1: shows a diagrammatic view of a specific gravity meter, and density transducer which may be used in the novel method according to the present invention.

Shown in FIG. 1, is a schematic view of a type 3098 in-line gas specific gravity (SG) meter as manufactured by Mobrey Limited of Slough, UK and branded by Micro Motion Inc, a division of Emerson Process Management, USA. This meter incorporates a type 7812 vibrating cylinder gas density transducer. The combined instrument can be calibrated to provide outputs of both gas molecular weight (M) and relative density ($\rho_{rel}$). Generally users of such instruments only calibrate the 3098 for one of these two properties. A characteristic of this invention is that the instrument is calibrated for, and used to measure, both properties.

The parameters that customers are most interested in when measuring methane-rich gases are:
a. gas density ($\rho_g$)
b. gas base density ($\rho_{base}$)
c. temperature (T)
d. pressure (P)
e. molecular weight (M)
f. line compressibility ($Z_{line}$)
g. base compressibility ($Z_{base}$)
h. % inerts (i.e. % nitrogen and % carbon dioxide)
i. Calorific value (CV)
j. Wobbe Index (WI)
k. relative density ($\rho_{rel}$)

In describing this invention, the following definitions will apply:
Gas Density: The mass of gas per unit volume at the actual pressure and temperature conditions being experienced (i.e. Line
Base Density: Also referred to as Standard Density or Normal Density, this is the density of a gas at standard conditions of temperature and/or pressure (e.g. 1 atm, 15.556° C.; or 1 Bar, 20° C.).
Relative Density: Ratio of density of a gas to the density of air, where the densities of both gases are taken at identical conditions of pressure and temperature.
Specific Gravity: The ratio of molecular weight of a gas to the molecular weight of dry air (Molecular weight of dry air=28.96469 g/mol)

As stated above, the CV of a methane-rich gas can be calculated by the expression:

$$CV = 0.02035 + (0.00197 - [0.000329 \times \% CO_2 + 0.000217 \times \% N_2])/SG \quad (1)$$

Using the type 3098 meter we can measure SG and in addition, using readily available instrumentation such as a near infrared monitor, we can accurately establish % $CO_2$. One aspect of the present invention is that we have established an accurate method of calculating % $N_2$ using data also collected during operation of the 3098 meter. This addresses the cost and time delay in directly measuring $N_2$ content using, for example, a gas chromatograph.

We have established that there is a relationship between $N_2$ content and base density ($\rho_{base}$), base compressibility ($Z_{base}$), Molecular weight (M) and $CO_2$ content according to the expression:

$$\% N_2 = A + B \times \rho_{base} + C \times Z_{base} + D \times M + E \times \% CO_2 \quad (2)$$

where A, B, C, D & E are constants.

Referring now to FIG. 3 this is a table of data which was obtained by conventional techniques and which was used during validation of the 3098. The data applies to different gases obtained from the named fields in Europe. As can be seen, the base densities and gas compositions vary considerably. By applying regression analysis to this data, we can find the constants A, B, C, D, & E. This process gives us:
A=15698.494
B=6966.401
C=−15876.507
D=−285.6609
E=−3.37234

As stated above, the above constants are derived from base data gathered from European oil/gas fields. We have established that fields in different geographical regions may produce quite different base data. By way of example, in the USA region using AGA8 data the constants, whilst still calculated according to expression (2), the constants become:
A=17151.34575
B=2173.4844875
C=17100.2863
D=97.239611
E=−1.176132655

For some fields data given may include % $O_2$ although in many fields producing methane-rich gases, the $O_2$ content of the gas is effectively zero. However, if $O_2$ data is available, the nitrogen content can be determined according to the expression:

$$\% N_2 = A + B \times \rho_{base} + C \times Z_{base} + D \times M + E \times \% CO_2 + F \times \% O_2 \quad (2a)$$

In this event, F is also a constant and, as with the other constants mentioned above, can be determined by applying regression analysis to data which includes $O_2$ content.

It should be stressed that, in the event that % $O_2$ data is not available, expression (2) still gives a useful and valuable indication of % $N_2$ content.

As indicated in expressions (2) and (2a), before we can calculate % $N_2$, we need to determine the values of $\rho_{base}$ and $Z_{base}$ for the gas undergoing measurement. These can be established using the 3098.

% $CO_2$ and, if applicable % $O_2$, can be established by using a near infrared technique.

Figure 2:
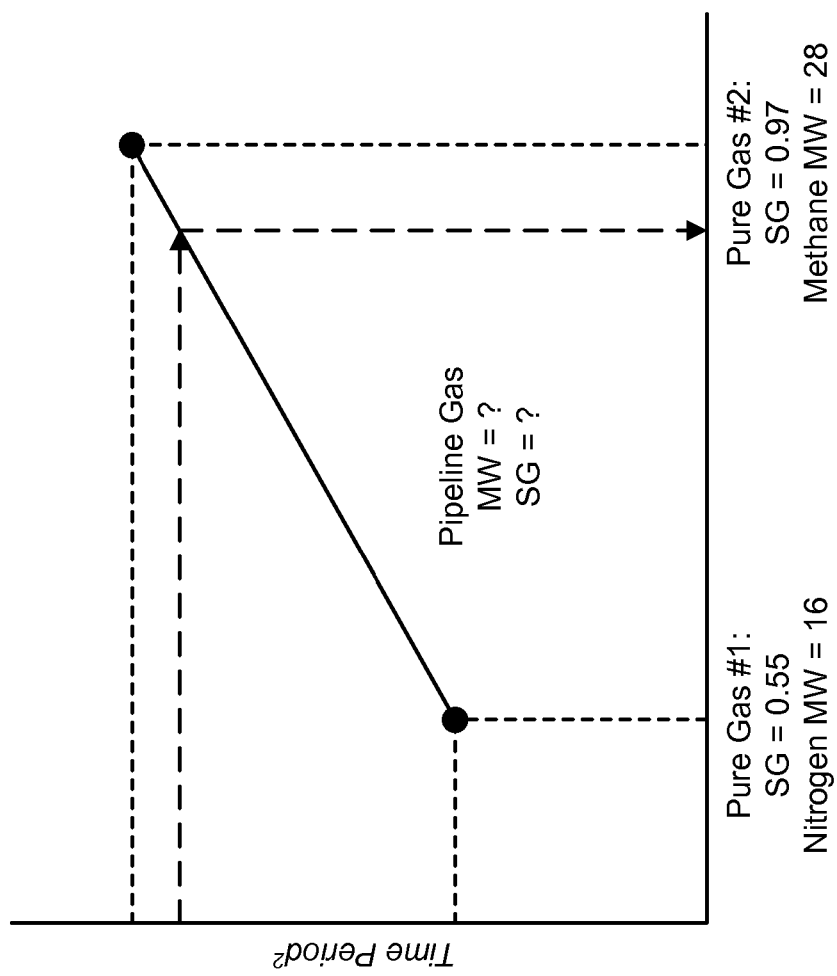
FIG. 2: shows a plot illustrating one calibration of the instrument shown in FIG. 1.

The first step in the use of the 3098 is calibration. Given that the gas density transducer is a resonating device, squaring the time period gives an output which is directly proportional to both density and molecular weight. Referring to FIG. 2, this illustrates calibration for molecular weight (M). The same process is followed when calibrating for relative density ($\rho_{rel}$). In both cases two pure gases with known M and known 92 $_{rel}$ are passed through the instrument and the time period output from the gas density transducer then squared and recorded. The two pure calibration gases are chosen to be those that best represent the properties of the gas mixture being measured—i.e. typically the two largest components of the mixture. As illustrated, the two calibration gases used are pure methane and pure nitrogen.

Thus, after such calibration, by measuring and squaring the time period output of the gas density transducer when pipeline gas is passed through the 3098, the relative density and molecular weight of that gas can be directly measured.

The principle of operation of the type 3098 SG meter relies on conditioning the measured gas in a way that the indicated density ($\rho$) is proportional to molecular weight (M).

Considering the underlying theory:

$$\rho = \frac{Mp}{RTZ} \quad (3)$$

where $p$ = pressure,
$T$ = temperature,
$\rho$ = gas density,
$R$ = gas constant and
$Z$ = line compressibility
and $$\rho_{rel} = \frac{\rho_{gas}}{\rho_{air}} \quad (4)$$

(at base conditions)

In the use of the 3098 the pressure and temperature of the pipeline gas is equalized with the reference gas. Thus (3) & (4) can be combined to give:

$$\rho_{rel} = \frac{M_g}{M_{air}} \times \frac{Z_{air}}{Z_g}$$

(at base conditions)

Now we can measure $\rho_{rel}$ and $M_g$ directly from the 3098 instrument, and we know $M_{air}$ and $Z_{air}$ (at base conditions) as these are constants. We can thus derive $Z_g$ at base conditions.

Finally, we need to establish $\rho_{base}$ of the gas being measured. This can be established according to either of the following alternatives.

Alternative 1

We know:

$$\rho = \frac{Mp}{RTZ}$$

or $$\rho_{base} = \frac{M_g P}{RTZ}$$

where P, R & T are constants.

Thus $\rho_{base}$ can be directly obtained from the double-calibrated 3098 instrument.

Alternative 2

This alternative involves a third calibration of the 3098 instrument, the third calibration property being gas density or $\rho_g$.

$$\rho_{base} = \rho_g \times \frac{P_{base}}{P} \times \frac{T}{T_{base}} \times \frac{Z}{Z_{base}} \quad (5)$$

where $P_{base}$, $T_{base}$ & $Z_{base}$ are values of pressure, temperature and compressibility at base conditions; and $\rho_g$, P, T & Z are values of gas density, pressure, temperature and compressibility at measurement conditions.

and we know:

$$\rho = \frac{M_g P}{RTZ}$$

so we can derive a value of Z to apply to (5) above and thus establish $\rho_{base}$.

This gas density calibration is performed in the manufacturing facility using a single pure gas ($N_2$)

We thus have all the variables needed to satisfy equation (2) and, thereby, establish % $N_2$. The value thus obtained can be fed into equation (1) to give CV.

Once we have a computation of CV we can derive Wobbe Index (WI) since $$WI = \frac{CV}{\sqrt{SG}}$$

It will be appreciated by those skilled in the art that various modifications of that which is described above is possible without departing from the scope of the invention. By way of example only, constant A in equation (2) above could be trimmed or refined from time to time by separately measuring % $N_2$ using a sampling technique (e.g. GC) and using that measurement to refine the calculation made according to a far more rapid time scale inherent in the claimed method.

It will thus be appreciated that the present invention, at least in the case of the embodiment described, provides a method of double-calibrating a 3098 specific gravity instrument which, in combination with a readily available $CO_2$ measurement meter, can give fast and accurate measurements of both Calorific Value and Wobbe Index. A combination of 3098, $CO_2$ meter, and novel calibration described above can give outputs of CV in the order of 5-10 seconds as opposed to the typical response time of around 7 minutes when using a gas chromatograph. Thus the present invention could be used in gas blending applications and is ideal for custody transfer applications.

The invention claimed is:

1. A method of determining the energy content of a methane-rich gas mixture comprising:
    forming a calibrated specific gravity meter by calibrating the specific gravity meter to measure both molecular weight and relative density in addition to providing an indication of specific gravity;
    using the calibrated specific gravity meter to measure a molecular weight M, a relative density and a specific gravity; and
    using the molecular weight M, the relative density and the specific gravity measured by the calibrated specific gravity meter to determine energy content of a methane-rich gas mixture as:

CV=0.02035+(0.00197−[0.000329×Mco2+0.000217× Mn2])/SG where CV=calorific value; Mco2=% CO2 content; Mn2=% N2 content and SG is specific gravity, wherein the % nitrogen content is derived according to the expression:

$$\% \ N2 = A + B \times \rho_{base} + C \times Z_{base} + D \times M + E \times \% \ CO2$$

where: $\rho_{base}$ is base density, $Z_{base}$ is base compressibility, M is the molecular weight and A, B, C, D, & E are constants.

2. A method as claimed in claim 1 wherein the constants A, B, C, D and E are determined from historical data obtained from varied sources of methane-rich gas mixtures.

3. A method as claimed in claim 2 wherein the constant A is refined from time to time using a sampling technique which reduces said methane-rich gas mixture into its constituent parts.

4. A method as claimed in claim 2 including determining % carbon dioxide content using a near infrared meter.

5. A method as claimed in claim 1 wherein the constant A is refined from time to time using a sampling technique which reduces said methane-rich gas mixture into its constituent parts.

6. A method as claimed in claim 1 including determining % carbon dioxide content using a near infrared meter.

7. A method of determining the energy content of a methane-rich gas mixture comprising:
forming a calibrated specific gravity meter by calibrating the specific gravity meter to measure both molecular weight and relative density in addition to providing an indication of specific gravity;
using the calibrated specific gravity meter to measure a molecular weight M, a relative density and a specific gravity; and
using the molecular weight M, the relative density and the specific gravity measured by the calibrated specific gravity meter to determine energy content of a methane-rich gas mixture as:

$$CV = 0.02035 + (0.00197 - [0.000329 \times Mco2 + 0.000217 \times Mn2])/SG$$

where CV=calorific value; Mco2=% CO2 content; Mn2=% N2 content and SG is specific gravity, wherein if % O2 data is available, the % nitrogen content is derived according to the expression:

$$\% \ N2 = A + BX \rho_{base} + CXZ_{base} + DXM + EX \ \% \ CO2 + FX \ \%O2$$

where: $\rho_{phase}$ is base density, $Z_{base}$ is base compressibility, M is molecular weight and A, B, C, D, E & F are constants.

8. A method as claimed in claim 7 wherein the constants A, B, C, D, E and F are determined from historical data obtained from varied sources of methane-rich gas mixtures.

9. A method as claimed in claim 8 wherein the constant A is refined from time to time using a sampling technique which reduces said methane-rich gas mixture into its constituent parts.

10. A method as claimed in claim 8 including determining % carbon dioxide content and % oxygen content using a near infrared meter.

11. A method as claimed in claim 7 wherein the constant A is refined from time to time using a sampling technique which reduces said methane-rich gas mixture into its constituent parts.

12. A method as claimed in claim 7 including determining % carbon dioxide content and % oxygen content using a near infrared meter.

* * * * *